United States Patent [19]

DeLuca et al.

[11] Patent Number: 5,354,744

[45] Date of Patent: * Oct. 11, 1994

[54] SIDE CHAIN UNSATURATED 1 ALPHA-HYDROXYVITAMIN D ANALOGS

[75] Inventors: Hector F. DeLuca, Deerfield; Heinrich K. Schnoes; Kato L. Perlman, botho of Madison, all of Wis.

[73] Assignee: Wisconsin Alumni Research Foundation, Madison, Wis.

[ * ] Notice: The portion of the term of this patent subsequent to Oct. 5, 2010 has been disclaimed.

[21] Appl. No.: 999,537

[22] Filed: Dec. 31, 1992

Related U.S. Application Data

[63] Continuation of Ser. No. 488,465, Feb. 26, 1990, abandoned, which is a continuation of Ser. No. 187,675, Apr. 29, 1988, abandoned.

[51] Int. Cl.$^5$ .......................... H61K 31/59; C07J 9/00
[52] U.S. Cl. ........................................ 514/167; 552/653
[58] Field of Search .................... 514/167; 552/653

[56] References Cited

U.S. PATENT DOCUMENTS

| | | | |
|---|---|---|---|
| 4,225,596 | 9/1980 | DeLuca | 514/167 |
| 4,230,701 | 10/1980 | Holick et al. | 514/167 |
| 4,689,180 | 8/1987 | DeLuca et al. | 514/167 |
| 4,717,721 | 1/1988 | DeLuca et al. | 514/167 |

OTHER PUBLICATIONS

CA 113: 78822r, Calverley et al., 1990.

*Primary Examiner*—Marianne M. Cintins
*Assistant Examiner*—Kimberly R. Jordan
*Attorney, Agent, or Firm*—Andrus, Sceales, Starke & Sawall

[57] ABSTRACT

This invention provides novel vitamin D-related compounds characterized by extended unsaturated side chain structures. Such compounds exhibit increased activity in arresting the proliferation and promoting the differentiation of malignant cells with only minimal calcemic activity and thus represents new therapeutic agents applicable and uniquely useful in differentiation therapy of malignant diseases. The activity characteristics of these compounds provide the basis of a method for the treatment of neoplastic diseases, specifically leukemoid diseases.

16 Claims, No Drawings

SIDE CHAIN UNSATURATED 1 ALPHA-HYDROXYVITAMIN D ANALOGS

This invention was made in the course of work supported by grants or awards from the Department of Health and Human Services. The Government has certain rights in this invention.

This application is a continuation of Ser. No. 07/488,465 filed Feb. 26, 1990, now abandoned which is a continuation of copending application Ser. No. 07/187,675 filed Apr. 29, 1988, now abandoned.

This invention relates to novel vitamin D compounds which are specifically active in Inducing the differentiation of malignant cells to normal cells. More specifically, this invention relates to side chain unsaturated and side chain extended analogs of $1\alpha$, 25-dihydroxyvitamin $D_3$ (1,25-$(OH)_2D_3$), which show selectivity of action as antineoplastic agents by virtue of increased activity in differentiating malignant cells and much reduced activity on calcium metabolism.

BACKGROUND

The activity of the D vitamins (vitamins $D_3$ or $D_2$) in regulating calcium metabolism and normal bone growth and development is known to require metabolism of parent vitamin to certain hydroxylated forms. Specifically, it has been established that $1\alpha$, 25-dihydroxyvitamin $D_3$ (1,25-$(OH)_2D_3$), the dihydroxylated metabolite normally formed from vitamin $D_3$ in the animal or human, is the active species responsible for stimulating calcium transport in the intestine, and calcium resorption from bone (bone mobilization), thereby regulating the overall blood calcium level of the organism. (These calcium-related activities of vitamin D metabolites or analogs will, in the following description, be referred to collectively as the 'calcemic activity' or 'calcemic action' of the compounds.) Certain structural analogs of 1,25-$(OH)_2D_3$, such as for example, $1\alpha$-hydroxyvitamin $D_3$, $1\alpha$-hydroxyvitamin $D_2$, 1,25-dihydroxyvitamin $D_2$, or fluoro-substituted derivatives of 1,25-$(OH)_2D_3$, are also known as highly active calcemic agents, and as a result 1,25-$(OH)_2D_3$ and its active analogs have been used, or proposed, as pharmaceuticals in the propylaxis or treatment of various calcium metabolism and bone disorders, such as renal osteodystrophy, vitamin D-resistant rickets, or osteoporosis and related diseases.

More recently, it has been discovered that 1,25-$(OH)_2D_3$, in addition to its well-known 'calcemic action' discussed above, also expresses other biological functions. For example, it has been found that 1,25-$(OH)_2D_3$ and closely related analogs ($1\alpha$-OH-$D_3$, 1,25-$(OH)_2D_2$, fluoro-substituted analogs, etc.) are capable of inducing cellular differentiation [Abe et al., Proc. Natl. Acad. Sci. USA 78, 4990 (1981); Honma et al., Proc. Natl. Acad. Sci USA 80, 201 (1983)]. Specifically, 1,25-$(OH)_2D_3$ and its analogs has been shown to inhibit the proliferation of malignant cells grown in culture (e.g. human leukemia cells) and induce their differentiation to normal macrophage-type cells. (These types of activities will henceforth be referred to collectively as the "differentiation activity" of vitamin D compounds.) Because of their remarkable potency as differentiation-inducing agents, these vitamin D derivatives are potentially useful for anticancer agents, and their use for the treatment of human leukemias has indeed been proposed (Suda et al., U.S. Pat. No. 4,391,802). However, even though these compounds are highly effective in differentiating malignant cells in culture, their equally high calcemic action in vivo limits or precludes their use as practical anticancer agents. Thus, 1,25-$(OH)_2D_3$ or its fluorinated derivatives are exceedingly potent cell differentiation agents, but they also are the most potent compounds with respect to calcemic activity, and at the levels required in vivo for effective use as anticancer (e.g. antileukemic) agents, these same compounds can produce dangerously elevated blood calcium levels by virtue of their inherent calcemic activity. Other known vitamin D derivatives show a similar correspondence between differentiation activity and calcemic activity, and their practical use as potential anticancer agents, therefore, is subject to the same limitations and hazard.

These observations clearly indicated a need, and have stimulated a search, for compounds with greater specificity and selectivity of action as anticancer agents, i.e. for compounds with an improved differentiation/calcemic activity ratio, and recent work has, indeed, led to the preparation of several vitamin D analogs with enhanced differentiation activity. It has been found for example, that certain 1,25-$(OH)_2D_3$ homologs, in which the side chain is extended by one carbon (either within the chain or at its terminus) exhibit a markedly higher differentiation activity (about 10 times) for leukemia cells in culture than 1,25-$(OH)_2D_3$ itself [DeLuca et al., U.S. Pat. No. 4,717,721; Ostrem and DeLuca, Steroids 49, 73–102 (1988); Ostrem et al., J. Biol. Chem. 262, 14864 (1987)]. However, these homologs are still extremely potent calcemic agents, exhibiting calcemic activities approximately equal to that of 1,25-$(OH)_2D_3$. These compounds therefore are characterized by an improved differentiation/calcemic activity ratio, but they do not overcome the problem of the undesired potent calcemic action discussed above. Other vitamin D-related compounds, reported to have preferential differentiation activity, have been prepared [see Ostrem et al., supra; Kubodera et al. Chem. Pharm. Bull. 34, 2286–89 (1986); Ikekawa et al. Chem. Pharm. Bull 35, 4362 (1987)], but these are structurally distinct and different from the compounds of the present invention.

SUMMARY OF THE INVENTION

Vitamin D-related compounds have now been found which exhibit a desired and very advantageous activity pattern in terms of their differentiation vs. calcemic responses. These new vitamin analogs exhibit very pronounced activity in inhibiting the proliferation of malignant cells and inducing their differentiation to normal monocyte-type cells (similar to or greater than that of 1,25-$(OH)_2D_3$), but they are much less active than 1,25-$(OH)_2D_3$, as far as their calcemic action is concerned. Thus, these new compounds exhibit a dramatically improved differentiation/calcemic activity ratio, and by virtue of this characteristic, the compounds represent preferred agents for the treatment of neoplastic diseases. In being highly active in inducing differentiation, and much less active as calcemic agents, these compounds can be administered without inducing excessively elevated blood calcium levels, thereby overcoming a major practical problem associated with high calcemic activity.

The novel compounds are characterized structurally as side chain unsaturated homologs of 1,25-$(OH)_2D$ in which the side chain is elongated by insertion of two or three methylene units into the carbon chain. They may be represented, therefore, by the following general structure:

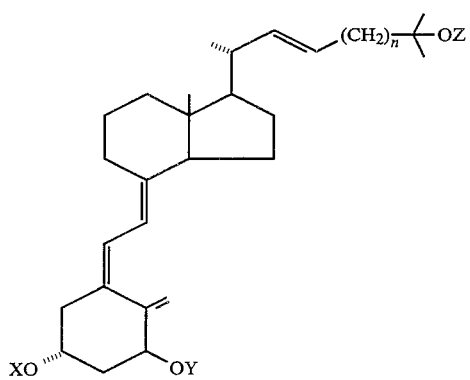

where X, Y and X, which may be the same or different, are selected from the group consisting of hydrogen and a hydroxy-protecting group and where n has the values 3 or 4.

Specific and preferred examples of these compounds are 24-dihomo-1,25-dihydroxy-22-dehydrovitamin $D_3$, i.e. the compound shown above, where X, Y and Z are hydrogen and n equals 3, and 24-trihomo-1,25-dihydroxy-22-dehydrovitamin $D_3$, i.e. the compound having the structure shown above, where X, Y and Z are hydrogen and n equals 4.

It is apparent that these new compounds are related to the side chain unsaturated 24-homo-vitamin D compound shown in U.S. Pat. No. 4,717,721. However, the new compounds have distinguishing structural and biological characteristics. Structurally, the distinguishing feature is an unsaturated side chain homologized by insertion of two or three methylene units, and biologically, the compounds are highly potent cell differentiating agents, without, or with much reduced, calcemic activity.

Preparation of New Compounds

The synthesis of examples of the new compounds of this invention is shown in Schemes 1, 2 and 3. Scheme 1 shows the preparation of the required 1α-hydroxyvitamin D-22-aldehyde intermediate, which, when coupled with the appropriate alkylphenyl sulfone side chain unit, as shown in Process Scheme 2, provides the desired vitamin D homologs (e.g. compounds (25) and (26), respectively). Scheme 3 illustrates the preparation of the alkylphenylsulfone units required for side chain coupling. Experimental details for the chemical process steps depicted in the schemes are provided in the specific examples which follow. Compound designations by Arabic numerals (e.g. compound 1, 2,

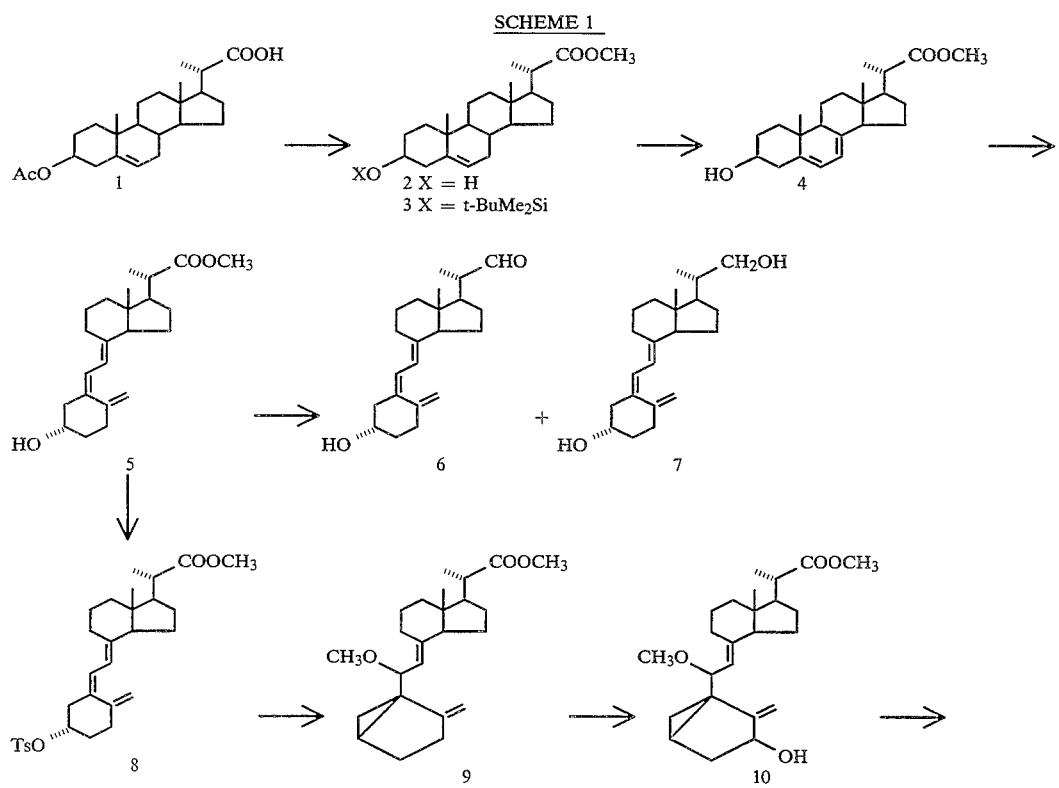

SCHEME 1

-continued
SCHEME 1
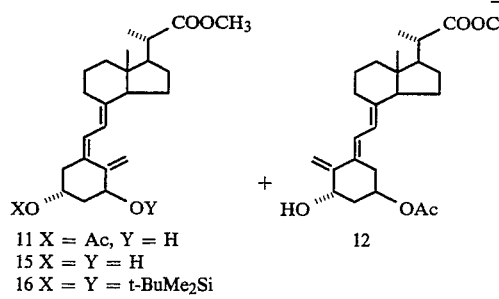
11 X = Ac, Y = H
15 X = Y = H
16 X = Y = t-BuMe₂Si
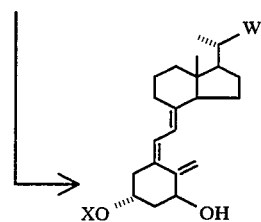
12
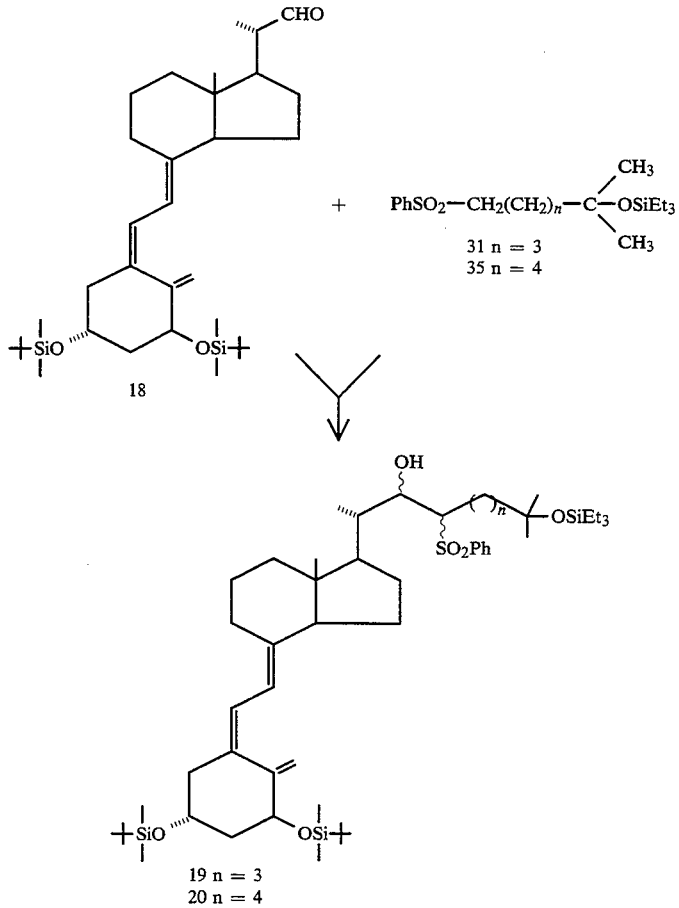
13 X = Y = H; W = CHO
14 X = Y = H; W = CH₂OH
17 X = Y = t-BuMe₂Si; W = CH₂OH
18 X = Y = t-BuMe₂Si; W = CHO
SCHEME 2
31 n = 3
35 n = 4
19 n = 3
20 n = 4

-continued
SCHEME 2

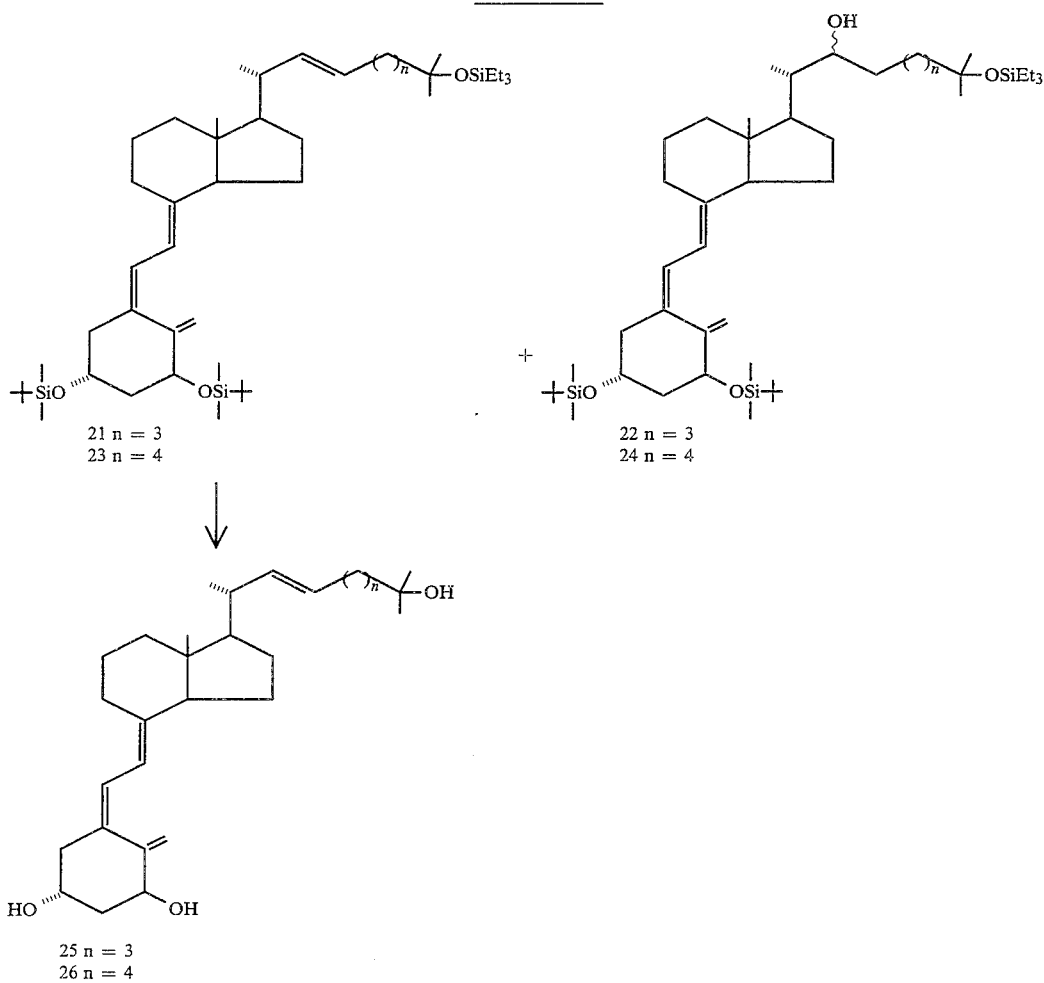

21 n = 3
23 n = 4

22 n = 3
24 n = 4

25 n = 3
26 n = 4

SCHEME 3

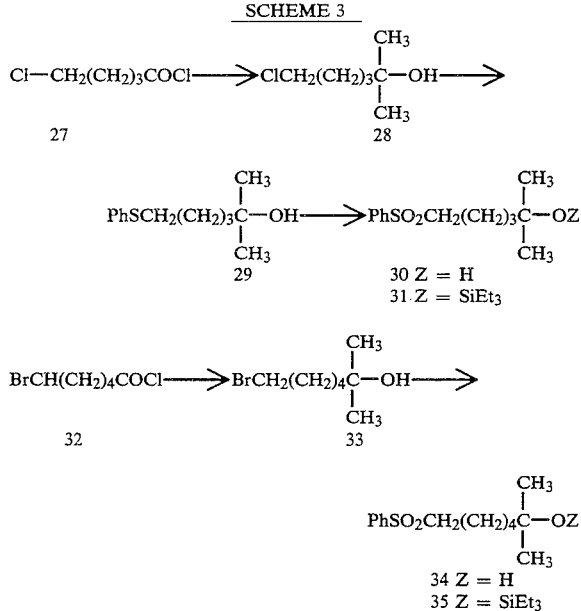

3, etc.) as used in these examples refer to the structures so numbered in the schemes.

General Procedures

3β-Acetoxy-22,23,-bisnor-5-cholenic acid (1) was purchased from Steraloids (Wilton, N.H.). All other chemicals were of the best quality from commercially available sources. Solvents were purified by standard methods.

Thin-layer chromatography (TLC) was performed using precoated aluminum silica gel sheets with UV indicator from EM Science (Gibbstown, N.J.). Solvent systems used: A: chloroform-ethanol 85:15 (v/v); B: hexane-ethyl acetate 1:1 and C: hexane-ethyl acetate 3:1.

High-performance liquid chromatography (HPLC) was performed using a Waters Associates liquid chromatograph equipped with a Model 6000A solvent delivery system, a Model 6 UK Universal injector and a Model 450 variable wavelength detector. Zorbax-Sil (Phenomenex) columns (6.2 mm×25 cm and 10 mm×25 cm) were used. Solvent systems: A: 3% 2-propanol in hexane; B: 2% 2-propanol in hexane; C: 6% 2-propanol in hexane; D: 10% 2-propanol in hexane; E: 20% 2-propanol in hexane. Silica gel Sep-Pak (Waters Associates) cartridges were used for the prefiltration of HPLC samples.

Electron impact mass spectra (MS) were recorded at 70 eV with Kratos MS-50 TC Mass Spectrometer equipped with Kratos DS-55 Data System.

Ultraviolet (UV) absorption spectra were recorded with a Hitachi Model 60-100 UV-Vis spectrophotometer.

Infrared spectra were recorded on a Nicolet MX-1 FT–IR spectrometer using films of oily substances or carbon tetrachloride solutions.

Proton magnetic resonance spectra ($^1$H-NMR) were taken with Bruker 270, 400 or 500 MHz spectrometers in CDCl$_3$ solutions containing tetramethylsilane (TMS) as internal standard.

EXAMPLE 1

Synthesis of protected C-22-aldehyde (Compound 18; Scheme 1)

This aldehyde is prepared according to the general procedure of Kutner et al. (Tet. Letters 28, 6129–32, 1987). Compound (1) (10 g) was dissolved in 420 mL of 5% KOH in methanol and the solution was stirred at ambient temperature for 15 min until none of the starting material was detected by TLC (solvent system A). To this solution, 160 mL of 10% sulfuric acid in methanol was added dropwise with stirring and the resulting suspension was diluted with 400 mL of 1% sulfuric acid in methanol. The mixture was heated under reflux for 48 h to complete the esterification (TLC, solvent system A). Compound (2) (the ester) was extracted with ethyl acetate. The organic phase was washed with 5% NaHCO$_3$, saturated NaCl and dried over magnesium sulfate. The product, compound (2), (9.0 g, 88%) was used for the next step without further purification.

To a solution of compound (2) (4.4 g, 12 mmol) in 135 mL of dry dimethylformamide (DMF) was added imidazole (3.6 g, 52.8 mmol), followed by tert-butyldimethylsilyl chloride (4.0 g, 26.4 mmol). The solution was stirred at room temperature for 5 min until the bulky precipitate was formed and then stirring was continued for additional 15 min. The reaction mixture was extracted with hexane (400 mL), washed with water, saturated NaCl solution, and dried over magnesium sulfate. Evaporation of the solvent provided TLC pure (solvent system B) product, compound (3) (5.3 g, 91%), that was used for the next step without further purification. An analytical sample was obtained by flash chromatography using 2% ethyl acetate in hexane.

A mixture of compound (3) (1.0 g, 2.1 mmol), dibromantin (0.42 g, 1.5 mmol) and anhydrous sodium bicarbonate (0.91 g, 10 mmol) in 20 mL of hexane was heated under reflux in a nitrogen atmosphere for 30 min until no starting compound (3) was detected (TLC, system C). The precipitate was filtered off and the solution dried down under reduced pressure. The residue was redissolved in 5 mL of anhydrous THF, tetrabutylammonium bromide (0.06 g, 0.19 mmol) was added, and the mixture stirred at room temperature for 30 min under nitrogen. A solution of tetrabutylammonium fluoride (10 mL, 1M in THF) was then added, followed by 0.7 mL of s-collidine, and the mixture was stirred under nitrogen at room temperature for 1 h. Another 5 mL of tetrabutylammonium fluoride solution was added and stirring was continued for 3 h. Ether (50 mL) was added and the organic phase was washed with water, cold 1N HCl, 10% NaHCO$_3$ and dried over anhydrous magnesium sulfate. The product, compound dissolved in benzene, was chromatographed on silica gel 70–230 mesh (30 g). Compound (4) (0.44 g, 58%) was eluted using ethyl acetate in hexane. An analytical sample was obtained by HPLC (system A, R$_V$77 mL): IR (film) 1737, 1604, 1495, 1082, 1030 cm$^{-1}$; UV (3% 2-propanol in hexane) $\lambda_{max}$ 262 nm ($\epsilon$7,000), 272 nm ($\epsilon$ 9,800) $\lambda_{max}$ 282 nm ($\epsilon$10,500) $\lambda_{max}$ 293 ($\epsilon$6,000); $^1$H NMR (CDCl$_3$) $\delta$0.54 (3H, s, 18-CH$_3$), 0.94 (3H, s, 19-CH$_3$), 1.22 (3H, d, J=6 Hz, 2-CH$_3$), 3.6 (1H, m, 3H), 3.68 (3H, s, CO$_2$CH$_3$), 5.42 (1H, m, 6-H), 5.58 (1H, m, 7-H); MS m/z (relative intensity) 358 (61), 340 (12), 325 (100), 299 (68), 271 (7), 253 (17), 237 (26), 211 (27), 143 (72), 119 (35).

A solution of compound (4) (830 mg, 2.3 mmol) in 350 mL of benzene-ethyl ether, 1:4 (v/v) was irradiated with stirring under nitrogen in a water-cooled quartz immersion well equipped with a nitrogen bubbler and a Vycor filter using Hanovia 608A36 medium-pressure UV lamp for 40 rain (4×10 rain). The reaction was monitored by HPLC using 2% 2-propanol in hexane at 265 nm. The solution was dried down under reduced pressure, redissolved in 100 mL of absolute ethanol and heated under reflux in a nitrogen atmosphere for 3 h. Then the solution was concentrated, redissolved in 1 mL of 10% ethyl acetate in hexane and chromatographed on silica gel 70–230 mesh (30 g). Vitamin ester (5) (298 mg, 36%) was eluted using a mixture of 15% ethyl acetate in hexane. An analytical sample was obtained by HPLC (system B, R$_V$94 mL): IR (film) 1738 cm$^{-1}$; UV (EtOH) $\lambda_{max}$ 264 nm, $\lambda_{min}$ 228 nm; $^1$H NMR (CDCl$_3$) $\delta$, 0.56 (3H, s, 18-CH$_3$), 1.20 (3H, d, J=7 Hz, 21-CH$_3$), 3.66 (3H, s, CO$_2$CH$_3$), 3.95 (1H, m, 3-H), 4.80 (1H, d, J=1.2 Hz, 19Z-H), 5.05 (1H, d, J=1.2 Hz, 19E-H), 6.03 (1H, d, J=11 Hz, 7-H), 6.23 (1H, d, J=11 Hz, 6-H); MS m/z (relative intensity), M+358 (45), 340 (9), 325 (45), 299 (22), 253 (19), 237 (18), 136 (60), 118 (100).

A solution of compound (5) (10 mg, 0.028 mmol) in 5 mL of dry toluene was cooled under nitrogen to −70° C. in a dry ice-acetone bath. To this solution, diisobutylaluminum hydride (DIBAL-H, 50 μL, 25% solution in toluene, 0.088 mmol) was added dropwise with stirring. The reaction mixture was stirred at −70° C. for 10 min and then methanol (2 mL) was slowly added. The mixture was allowed to warm up to room temperature, diluted with ethyl ether and washed with 5% HCl, 5% NaHCO$_3$, water, saturated NaCl and dried over anhydrous magnesium sulfate. Silica gel chromatography (15% ethyl acetate in hexane) afforded compound (6) (4.9 rag, 54%), with the following spectral data: MS: 328 (M+, 29), 310 (5), 295 (31), 269 (11), 253 (6), 136 (47), 118 (86), 29 (100); $^1$H-NMR (CDCl$_3$) $\delta$:0.59 (3H, s, 18-CH$_3$), 1.14 (3H, d, J=7 Hz, 21-CH$_3$), 4.0 (1H, m, 3-H), 4.81 (1H, d, J=1.2 Hz, 19E-H), 5.05 (1H, d, J=1.2 Hz, 19Z-H), 6.05 (1H, d, J=11 Hz, 7-H), 6.23 (1H, d, J=11 Hz, 6-H), 9.58 (1H, d, J=3.8 Hz, 22-H).

Further elution of the silica gel column with 5% 2-propanol in hexane yielded the C-22-alcohol, compound (7) (2.7 mg, 29%).

Compound (5) was converted into compound (8) by using p-toluenesulfonyl chloride in pyridine at 4° C. for 20 h. Compound (8) (102 mg, 0.2 mmol) dissolved in 2 mL of anhydrous dichloromethane was added to the methanol solution (15 mL) of anhydrous potassium bicarbonate (250 mg) with stirring at 55° C. The mixture was stirred under nitrogen at 55° C. for 24 h. The solvents were then removed under reduced pressure and the residue extracted with ether. The organic phase was washed with water and dried over anhydrous magnesium sulfate. The product, compound (9), was purified by silica gel chromatography using 20% ethyl acetate in hexane (50 mg, 68%).

Tert-butyl hydroperoxide (112 μL, 3.0M solution in toluene, 0.34 mmol) was added to a suspension of selenium dioxide (9 mg, 0.8 mmol) in 2 mL of dry methylene chloride. The mixture was stirred at room temperature under nitrogen until a clear solution was formed. Anhydrous pyridine (12 μL, 0.15 mmol) was then added followed by compound (9) (50 mg) dissolved in 2 mL of anhydrous dichloromethane. The mixture was stirred under nitrogen for 30 min. Cold 10% sodium bicarbonate (2 mL) was added and the mixture extracted with ether. The organic phase was washed with cold 10% sodium bicarbonate, ice water and dried over anhydrous magnesium sulfate. Silica gel chromatography (10–20% ethyl acetate in hexane) afforded 12.5 mg of compound (10). The product was then immediately dissolved in 0.5 mL of glacial acetic acid and the solution was heated at 55° C. with stirring under nitrogen for 15 min. The reaction mixture was poured over ice, extracted with ether and washed with ice-cold saturated sodium bicarbonate. The combined ether extracts were washed with water and dried over anhydrous magnesium sulfate. Analytical samples of (5Z,7E) and (5E,7E) isomers, (11) and (12), respectively were obtained by preparative HPLC in a ratio of 2.5:1.

Compound 11: HPLC, $R_V$ 68 mL; UV (EtOH) $\lambda_{max}$ 264 nm, $\lambda_{min}$ 227 nm, A264/A227=2.07; $^1$H NMR (CDCl$_3$) δ, 0.56 (3H, s (3H, d, J=6.5 Hz, 21-CH$_3$), 2.04 (3H, s, 3β-acetyl), 3.66 (3H, s, 22-CO$_2$CH$_3$), 4.4 (1H, m, 1-H), 5.2 (1H, m, 3-H), 5.01 (1H, br s, 19E-H), 5.34 (1H, br s, 19Z-H), 6.01 (1H, d, J=10 Hz, 7-H), 6.33 (1H, d, J=10 Hz, 6-H); MS m/z (relative intensity), 416 (M$^+$, 4), 356 (100), 338 (21), 251 (13), 134 (95). Compound 12: HPLC, $R_V$ 78 ml; UV (EtOH) $\lambda_{max}$ 267 nm, $\lambda_{min}$ 227 nm, A267/A227=3.51; $^1$H NMR (CDCl$_3$) δ, 0.56 (3H, s, 18-CH$_3$), 1.20 (3H, d, J-6.5 Hz, 21-CH$_3$), 2.04 (3H, s, 3β-OAc), 3.66 (3H, s, 22-CO$_2$CH$_3$), 4.5 (1H, m, 1-H), 5.3 (1H, m, 3-H), 4.99 (1H, br s, 19E-H), 5.13 (1H, br s, 19Z-H), 5.81 (1H, d, J=10 Hz, 7-H), 6.56 (1H, d, J=10 Hz, 6-H).

For large scale preparations, isomers (11) and (12) can also be effectively and advantageously separated by the maleic anhydride procedure described in U.S. Pat. No. 4,554,106.

Diisobutylaluminumhydride (15 μL, 1.5M solution toluene) was added with stirring to a solution of compound (11) (2 mg) in 0.5 mL of anhydrous toluene at −70° C. under nitrogen. The mixture was stirred at −70° C. for 10 min and 0.2 mL of methanol was slowly added to decompose the organometallic complex. The mixture was warmed up to room temperature and extracted with ethyl ether. The organic phase was washed with water and dried over anhydrous magnesium sulfate. Preparative HPLC, using a solvent system E afforded compound (13) and compound (14). Compound (13) gave the following spectral data: 344 (M$^+$, 22), 326 (13), 311 (2), 285 (4), 269 (4), 152 (29), 134 (100); $^1$H-NMR (CDCl$_3$) δ, 0.59 (3H, s, 18-CH$_3$), 1.15 (3H, d, J=7 Hz, 21-CH$_3$), 4.2 (1H, m, 3-H), 4.4 (1H, m, 1-H), 4.99 (1H, d, J=1.2 Hz, 19Z-H), 5.31 (1H, d, J=1.2 Hz, 19E-H), 6.02 (1H, d, J=11 Hz, 7-H), 6.36 (1H, d, J=11 Hz, 6-H), 9.56 (1H, d, J=4 Hz, 22-H).

A 0.1N solution of KOH in methanol (10 mL) was added to a stirred solution of compound (11) (100 mg, 0.24 mmol) in ethyl ether (10 mL). The resulting solution was stirred at room temperature for 90 min until no starting material was detected by TLC (solvent system B). Compound (15) was isolated by standard extraction procedure (ethyl acetate, saturated NaCl, anhydrous magnesium sulfate) to give colorless oil (86.2 mg, 96%).

A mixture of imidazole (250 mg, 3.6 mmol) and tert-butyldimethylsilyl chloride (250 mg, 1.6 mmol) in DMF (2 mL) was added to a stirred solution of compound (15) (86.2 mg, 0.23 mmol) in 4 mL of dimethylformamide. The resulting homogenous mixture was stirred for 15 min at 55° C. until no starting material was detected by TLC (solvent system B). The product was isolated by hexane extraction of the reaction mixture. Organic extract was washed with brine and dried over anhydrous magnesium sulfate. Hexane solution of the crude product was filtered through silica gel Sep-Pak cartridge to give compound (16) (136 mg, 98%). IR (film) 2974, 2930, 1736, 1447, 1286, 1258, 1150, 1085 cm$^{-1}$; UV (hexane) $\lambda_{max}$ 264 nm, $\lambda_{min}$ 227 nm, A264/A227=1.91; $^1$H NMR (CDCl$_3$), δ0.07 [12H, s, Si(CH$_3$)$_2$], 0.55 (3H, s, 18-CH$_3$), 0.86 [18H, s, C(CH$_3$)$_3$], 1.20 (3H, d, J=6.8 Hz, 21-CH$_3$), 3.65 (3H, s, 0-CH$_3$), 4.18 (1H, m, 3-H), 4.36 (1H, m, 1-H), 4.84 (1H, d, J=1.2 Hz, 19Z-H), 5.16 (1H, d, J=1.2 Hz, 19E-H), 5.96 (1H, d, J=11.2 Hz, 7-H), 6.19 (1H, d, J=11.2 Hz, 6-H); MS m/z (intensities normalized to m/e 248) 602 (M$^+$, 10), 470 (59), 413 (7), 338 (10), 248 (100).

Lithium aluminum hydride (25 mg, 0.65 mmol) was added to a stirred solution of compound (16) (136.2 mg, 0.23 mmol) in anhydrous THF (5 mL) under argon at 0° C. The suspension was stirred for 15 min at 0° C. and the excess of lithium aluminum hydride was decomposed by the dropwise addition of 10% water in THF. The suspension was diluted with 10 mL of THF and the stirring was continued for an additional 15 min at room temperature. The product was isolated by the standard extraction with ethyl acetate. Compound (17) was obtained as a colorless oil (118.4 mg) in 91% yield. IR (film) 3450, 2952 2886, 1447, 1258, 1105, 1085, 834 cm$^{-1}$; UV (EtOH) $\lambda_{max}$ 264 nm, $\lambda_{min}$ 227 nm, A264/A227=1.57; $^1$H NMR (CDCl$_3$) δ0.00 (12H, s, Si-CH$_3$), 0.53 (3H, s, 18-CH$_3$), 0.85 [18H, s, Si-C(CH$_3$)$_3$], 1.04 (3H, d, J=6.4 Hz, 21-CH$_3$), 3.37 and 3.63 (1H and 1H, each m, 22-CH$_2$), 4.17 (1H, m, 3-H), 4.35 (1H, m, 1-H), 4.84 (1H, br s, 19Z-H), 5.16 (1H, br s, 19E-H), 6.00 (1H, d, J=12.2 Hz, 7-H), 6.21 (1H, d, J=12.2 Hz, 6-H); MS M/z (intensities normalized to m/z 248), 574 (M+17) 442 (67) 383 (11) 308 (17) 248 (100).

A solution of oxalyl chloride (30 μL, 0.34 mmol) in 0.5 mL of dichloromethane was added dropwise to a stirred solution of DMSO (50 μL, 0.7 mmol) in 3 mL of dichloromethane at −60° C. under nitrogen. The resulting solution was stirred at −60° C. for 10 rain and the solution of compound (17) (27 mg, 0.05 mmol) in 1 mL of dichloromethane was slowly added. The mixture was stirred for 30 min at −60° C. Then 0.2 mL of triethylamine was added and the solution was stirred for another 5 min. The product, compound (18), was extracted with ethyl ether and the organic extract was washed with saturated NaCl and dried over anhydrous magnesium sulfate. Silica gel Sep-Pak filtration afforded TLC pure product (17 mg, 62%). IR (film) 2954, 2929, 2884, 2857, 1727, 1472, 1375, 1256, 1085, 909, 880, 835 cm$^{-1}$; NMR (CHCl$_3$) δ0.00 (12H, s, Si-CH$_3$), 0.60 (3H, s, 18-CH$_3$), 0.88 [18H, s, Si-C(CH$_3$)$_3$], 1.11 (3H, d, J=6.9 Hz, 21-CH$_3$), 4.23 (1H, m, 3-H), 4.43 (1H, m, 1-H), 4.93 (1H, br s, 19Z-H), 5.19 (1H, br s, 19E-H), 6.07 (1H, d, J=10.0 Hz, 7-H), 6.26 (1H, d, J=10.0 Hz, 6-H), 9.54 (1H, d, J=3 Hz, 22-H); UV (hexane) $\lambda_{max}$ 264 nm, $\lambda_{min}$ 227 nm, A264/A227=1.9; MS m/z (intensities relative to m/z 248) 572 (M+13) 440 (53), 383 (11) 308

(14) 248 (100); exact mass calculated for $C_{34}H_{60}O_3Si_2$ 572.4081, found 572.4117.

An improved yield of aldehyde (18) was obtained when the oxidation step was conducted under the following conditions: A solution of 15 μL (0.17 mmol) oxalyl chloride in 0.75 mL anhydrous dichloromethane was added dropwise to a stirred solution of 25 μL (0.36 mmol) dimethyl sulfoxide in 0.25 mL anhydrous dichloromethane at −60° C. under an argon atmosphere. After the mixture was stirred for 10 min at −60° C., the solution of 20.3 mg (0.035 mmol) of alcohol (17) in 0.5 mL of anhydrous dichloromethane was slowly added, and the flash rinsed with an additional 0.2 mL anhydrous dichloromethane. The mixture was stirred for 30 min at −60° C. and 0.3 mL (2.15 mmol) of triethylamine was added at −60° C. The mixture was stirred for 5 min and warmed to 0° C. and extracted with ether. The ether phase was washed with brine and dried (MgSO$_4$). Silica gel Sep-Pak filtration afforded (18) as a colorless oil which was purified by HPLC (Zorbax-Sil 9.4×25 cm, 10% EtOAc in hexane) to give the pure aldehyde (18) (19 mg, 96%); only a trace of alcohol was recovered (0.12 mg).

EXAMPLE 2

Side chain attachment: Synthesis of 24-dihomo-1α,25-dihydroxy-22-dehydrovitamin D$_3$ (compound 25, Scheme 2)

(a) preparation of hydroxysulfone (19)

To a stirred solution of 31 mg (84 μmol) 2-methyl-6-(phenylsulfonyl)-2-(triethylsilyloxy)-hexane (compound 31, Scheme 3) in 300 μL anhydrous tetrahydrofuran (containing 1.10 phenanthroline as indicator) under argon atmosphere at −78° C. was added 13 μL (90 μmol) diisopropylamine followed by 70 μL of n-BuLi (1.30 molar in hexane) (91 μmol). The solution was stirred under argon atmosphere at −78° C. for 30 min, then 6 mg of C-22-aldehyde (compound 18) (10 μmol) in 300 μL anhydrous tetrahydrofuran was added and stirred at −78° C. for 1 h. The mixture was decomposed by the addition of 1 mL of saturated NH$_4$Cl solution, warmed to 0° C., and extracted with ethyl acetate. The ethyl acetate was washed with water and brine, dried over anhydrous MgSO$_4$, filtered and evaporated. Preparation HPLC (Zorbax-Sil column 9.6×25 cm, Solvent system: 10% ethyl acetate in hexane) gave 0.6 mg unreacted aldehyde and 6.6 mg of the hydroxysulfone (19) as a mixture of epimers (77% yield).

24-Dihomo-1α, 25-dihydroxy-22-dehydro-vitamin D$_3$ (25)

A saturated solution of Na$_2$HPO$_4$ in methanol (1.0 mL) was added to a stirred solution of hydroxysulfone (19) (3.3 mg) in 1.0 mL of anhydrous tetrahydrofuran followed by powdered anhydrous Na$_2$HPO$_4$ (160 mg). The mixture was stirred under Argon for 30 min and cooled to 0° C. Fresh 5% sodium amalgam (ca. 400 mg) was then added and the mixture was stirred for 16 h at 5° C. The mixture was diluted with 5 mL hexane and stirring was continued for 15 min. Solvents were decanted and the solid material was washed with hexane (3×5 mL). Ice and saturated NaCl solution was added to the combined organic solution. The organic layer was separated and passed through a Sep-Pak cartridge in hexane. HPLC purification gave 2.0 mg (71%) protected Δ$^{22}$-24-dihomo-1,25-(OH)$_2$D$_3$ (21), and a small amount of the 22-hydroxylareal product (22) (Zorbax-Sil 9.4×25 column, 10% EtOAC in hexane). Protected triol (21) (2 mg) was dissolved in 1.0 mL of anhydrous THF and to this solution tetrabutylammonium fluoride in THF (50 μL), 1M solution) was added. The mixture was stirred under argon for 1 h at 50° C. Ether (8 mL) was then added and the organic phase was washed with saturated NaCl. Solvents were removed and the residue was dissolved in 10% 2-propanol in hexane and filtered through silica Sep Pak. HPLC (20% 2-propanol in hexane Zorbax-Sil 9.4 ×25 cm) gave 0.6 mg of the desired product, the dibomo compound (25). UV (EtOH) λ$_{max}$ 264 nm, λ$_{min}$ 228 nm, A264/A228=1.87; $^1$H NMR (CDCl$_3$), 0.55 (3H, s, 18-CH$_3$), 1.00 (3H, d, J=6.6 Hz, 21-CH$_3$), 1.23 (6H, s, 26,27-CH$_3$) 4.23 (1H, m, 3-H), 4.43 (1H, m, 1-H), 5.00 (1H, brs, 19Z-H), 5.32 (1H, brs, 19E-H), 5.29 (2H, m, 22H and 23H), 6.01 (1H, d, J=11.3 Hz, 7-H); MS m/z (relative intensity) 442 (M+, 15), 424 (23), 406 (33), 391 (7), 287 (11), 285 (10), 269 (27), 251 (23), 152 (33), 134 (100), 116 (6), 59 (20); exact mass calcd. for $C_{29}H_{46}O_3$ 442.3446, found 442.3441.

EXAMPLE 3

Side chain attachment: Synthesis of 24-trihomo-1α,25-dihydroxy-22-dehydrovitamin D$_3$ (compound 26, Scheme 2)

(a) Preparation of hydroxysulfone

To a stirred solution of 58 mg (151 μmol) 2-methyl 7(phenylsulfonyl)-2-(triethylsilyloxy)-heptane (compound 35, Scheme 3) in 500 μL anhydrous tetrahydrofuran (containing 1,10-phenanthroline as indicator) under argon atmosphere at −78° C. was added 23 μL (160 μmol) diisopropylamine followed by 106 μL n-BuLi (1.5 molar in hexane) (160 μmol). The solution was stirred under argon atmosphere at −78° C. for 30 min, then 7 mg of C-22-aldehyde (compound 18) (12 μmol) in 300 μL tetrahydrofuran was added and stirred for 1 h. The mixture was decomposed at that temperature by the addition of 1 mL of saturated NH$_4$Cl solution, warmed to 0° C. and extracted with ethyl acetate. The ethyl acetate was washed with water and brine, dried over anhydrous MgSO$_4$, filtered and evaporated. Preparative HPLC (Zorbax-Sil 9.4×25 cm, solvent system 10% ethyl acetate in hexane) gave 0.4 mg of unreacted aldehyde and 7.5 mg of the hydroxysulfone (20) as a mixture of epimers (78%).

(b) 24-trihomo-1,25-dihydroxy-22-dehydrovitamin D$_3$ (26)

A saturated solution of Na$_2$HPO$_4$ in ethanol (1.0 mL) was added to a stirred solution of the hydroxysulfone (20) (7.5 mg) in 1.0 mL of anhydrous tetrahydrofuran followed by powdered anhydrous Na$_2$HPO$_4$ (160 mg). The mixture was stirred under argon for 30 min and cooled to 0° C. Fresh sodium amalgam 5% (ca. 400 mg) was then added and the mixture was stirred for 16 h at 5° C. The mixture was diluted with 5 mL hexane and stirring was continued for 15 min. Solvents were decanted and the solid material was washed with hexane (3×5 mL). The combined organic phase was washed with brine, separated, dried and evaporated. The residue was passed through a Sep Pak cartridge in 10% ethyl acetate in hexane. HPLC purification gave 2.12 mg of protected Δ$^{22}$-24-trihomo-1,25-(OH)$_2$D$_3$ (23) and 1.33 mg 22-hydroxylated product (24) (Zorbax-Sil 9.4×25 column, 10% ethyl acetate in hexane). Compound 23 (2.1 mg) was dissolved in 1.0 mL of anhydrous tetrahydrofuran and to this solution 50 μL tetrabutylammonium fluoride in tetrahydrofuran (1M solution) was added. The mixture was stirred under argon for 1 h at 50° C. Ether was then added and the organic phase was washed with brine. The ether phase was dried over anhydrous MgSO4, filtered and evaporated. The residue was dissolved in 30% 2-propanol in hexane and passed through a Sep Pak. HPLC purification (20%, 2-propanol in hexane, Zorbax-Sil 9.4×25 cm column) gave the desired trihomo product, compound 26 (0.8 UV (EtOH) $\lambda_{max}$ 264 nm $\lambda_{min}$ 228, A264/A228 =1.81; $^1$H NMR: (CDCl3) 0.56 (3H, s, 18-CH3), 1.00 (3H, d, J=6.6 Hz, 21-CH3), 1.23 (6H, s, 26,27-CH3), 4.23 (1H, m, 3-H), 4.43 (1H, m, 1-H), 5.00 (1H, brs, 19Z-H), 5.32 (1H, brs, 19E-H), 5.29 (2H, m, 22H and 23H), 6.01 (1H, d, J=11.3 Hz, 7-H); MS m/z (relative intensity) 456 (M+) (11) 438 (50), 420 (30), 402 (8), 287 (10), 269 (23), 251 (23), 152 (35), 134 (100).

EXAMPLE 4

Synthesis of sulfone side chain units (Scheme 3)

(a) Preparation of sulfone side chain residue (32)

A solution of 4-chlorovaleryl chloride 27 (Aldrich; 3 g, 19.2 mmol) in anhydrous THF (25 mL) was added dropwise with vigorous stirring, over 30 min, under argon, to a solution of methylmagnesium bromide (12.9 mL of a 3M solution in ether) in 25 mL of dry THF at −10° C. The reaction mixture was then allowed to warm up to room temperature within 2 h, then quenched with water and neutralized with diluted hydrochloric acid. The mixture was extracted with ether, the combined organic layers were washed with water and dried with sodium sulfate. After removal of the solvent, the residue was distilled in vacuo to give chloro-alcohol 28 as a colorless liquid (2.1 g, 70%). Chloro-alcohol 28 (1.5 g, 10 mmol) in anhydrous dimethylformamide (5 mL) was then added to a stirred solution of thiophenol (1.32 g, 12 mmol) and potassium t-butoxide (1.32 g, 11.3 mmol) in anhydrous dimethylformamide (25 mL). The reaction mixture was stirred at room temperature overnight and the solution was partitioned between dichloromethane and water. The organic layer was washed with aqueous sodium carbonate, water and dried over anhydrous magnesium sulfate. The solvent was evaporated in vacuo and the crude oil was purified by silica gel flash chromatography with hexane-ethyl acetate. Sulfide 29 (2.2 g, 98%) was obtained as a colorless liquid. Sulfide 29 (1.01 g, 4.5 mmol) was then dissolved in dry dichloromethane (40 mL) and 3-chloroperbenzoic acid (2.5 g, 11.6 mmol; Aldrich 80–85%) was added in portions with stirring and occasional cooling. The reaction mixture was stirred for 2 h and then quenched with 10% sodium bicarbonate. The combined organic extracts were washed with aqueous sodium sulfite and brine and dried over magnesium sulfate. The solvent was removed in vacuo and the crude oil was purified by silica gel flash chromatography using hexane-ethyl acetate mixtures to afford sulfone 30 (1.1 g, 97%) as a colorless liquid. To a stirred solution of sulfone 30 (1.3 g, 5.1 mmol) and imidazole (1.5 g, 22.7 mmol) in dry dimethylformamide (50 mL), triethylsilyl chloride (1.15 g, 7.7 mmol) was added. The reaction mixture was kept at room temperature for 2 h and then diluted with dichloromethane. The mixture was washed with aqueous ammonium chloride solution and water. The organic layers were dried over sodium sulfate and the solvent removed in vacuo. The residue was purified by silica gel flash chromatography. Hexaethyldisiloxane was first eluted with hexane. The triethylsily-protected sulfone 31 (1.8 g, 97%) was eluted with hexane-ethyl acetate 9:1 as a colorless liquid: IR (neat): 3045, 2940, 1440, 1360, 1130, 1020 cm$^{-1}$; $^1$H NMR (400 MHz, CDCl3) δ0.518 (6H, q, J=6.2 Hz, Si-CH2), 0.899 (9H, t, J=6.2 Hz, Si-C-CH3) δ0.518 (6H, q, J=6.2 Hz, Si-CH2), 0.899 (9H, t, J=6.2 Hz, Si-C-CH3), 1.142 (6H, s, CH3), 1.307-1.462 (4H, m), 1.655-1.738 (2H, m, H-4), 3.080-3.122 (2H, m, H-2), 7.567 (2H, t, J=6.8 Hz, H-aryl meta), 7.648 (1H, t, J=6.8 Hz, H-aryl para), 7.916 (2H, d, J=6.83 Hz, H-aryl ortho); MS (EI, 70 eV): m/z (relative intensity) 372 (M+2) 341 (100), 229 (2), 227 (18), 173 (24), 103 (22), 75 (45), 55 (33).

(b) Preparation of sulfone side chain unit (35)

A solution of 6-bromohexanoyl chloride (32) (3.8 g, 2.8 mL, 18 mmol) in anhydrous tetrahydrofuran (10 mL) was added dropwise with vigorous stirring over 15–20 min under argon atmosphere to a solution of methylmagnesium bromide (14 mL of 3M solution in ether) in anhydrous tetrahydrofuran (15 mL) at −10° C. The mixture was stirred at room temperature for 2 h, cooled to 0° C. and carefully decomposed with 1:1 diluted hydrochloric acid. The mixture was extracted with ether, the combined organic layers were washed with water, dried over anhydrous magnesium sulfate and evaporated to give the bromo alcohol (33) as a colorless oil (3.6 g) (94%).

The bromo-alcohol (3.4 g, 16 mmol) was treated with benzene sulfinic acid sodium salt (3.3 g, 20 mmol) in anhydrous dimethylformamide at 70° C. for 4½ h. The mixture was poured on ice, extracted with dichloromethane, washed with 1N HCl, water, 10% NaHCO3 solution, dried over anhydrous MgSO4, filtered and evaporated to give the sulfone (34) which was purified by flash chromatography on silica gel and eluted with 40–50% ethyl acetate in hexane to obtain the sulfone containing some of the corresponding sulfinate ester (4.18 g, 98%) MS, m/z 270 (M+), 255 (M+-15), 77, 59.

To a stirred solution of the sulfone (34) (4 g, 14 mmol) and imidazole (3.8 g, 55 mmol) in anhydrous dimethylformamide (13 mL) triethylsilyl chloride (4.6 g, 5.1 mL, 30 mmol) was added. The reaction mixture was stirred at room temperature for 2 h, poured on ice water, extracted with ether, dried over anhydrous MgSO4, filtered and evaporated. The residue was purified by flash chromatography. Hexaethyldisiloxane was first eluted with hexane; 3% ethyl acetate in hexane eluted the sulfinate ester with some of the sulfone, and 10% ethyl acetate in hexane eluted the protected pure sulfone (35) (3,4 g, 60%). Anal. calcd. for $C_{20}H_{36}O_3SSi$ C, 62.45%, H, 9.43%, S 38.34% Found C, 61.97%, H, 9.45%, S, 8.33% MS, m/z (relative intensity) 355 (100) (M+-29), 227 (15), 173 (35), 103 (43), 75 (95), 55 (23), NMR (400 MHz, CDCl3), 0.54 (6H, q, J=7 Hz, Si-CH2), 0.94 (9H, t, J=8 Hz, Si-C-CH3), 1.15 (6H, s, CH3), 1.31-1.36 (4H, m), 3.08-3.12 (2H, m, H=2), 7.57 (2H, t, J=6.8 Hz, H-aryl-meta), 7.66 (1H, t), H-aryl para), 7.92 (2H, d, J=6.8 Hz, H-aryl ortho).

Biological Activity

The new homolog (25) was tested for both differentiation activity and calcemic activity, using established assays known in the art. The assay procedures and results obtained are described in more detail in the following examples.

EXAMPLE 5

Measurement of differentiation activity of dihomo compound (25) in HL-60 cells (Table 1).

Degree of differentiation of HL-60 cells (human leukemia cells) in response to test compounds was assessed by three different assays: NBT-reduction, phagocytosis and esterase activity. The first two assays were carried out according to the general procedure given by DeLuca et al. in U.S. Pat. No. 4,717,721. The third assay, measuring nonspecific acid esterase activity as a marker for differentiation, was conducted according to the method given in Sigma Kit No. 90 available from Sigma Chemical Corp., St. Louis, Mo. [see also Ostrem et al., Proc. Natl. Acad. Sci. USA 84, 2610–2614 (1987); Ostrem et al. J. Biol. Chem. 262, 14164–14171 (1987)]. Results are shown in Table 1, below. Data are presented as the percent of differentiated cells resulting from treatment with various concentrations of 1,25-$(OH)_2D_3$ (used as comparison standard) or vitamin D test compound.

TABLE 1

Comparison of Differentiation Activity of 1,25-$(OH)_2D_3$ and Side Chain Dihomo Compound in HL-60 Cells in Culture

| Compound Administered | Concentration (molar) | % Differentiated Cells | | |
|---|---|---|---|---|
| | | Esterase | Phago-cytosis | NBT |
| 1,25-$(OH)_2D_3$ | $1 \times 10^{-7}$ M | 91 ± 2 | 90 ± 3 | 90 ± 2 |
| | $1 \times 10^{-8}$ M | 61 ± 4 | 56 ± 2 | 55 ± 4 |
| | $1 \times 10^{-9}$ M | 30 ± 3 | 31 ± 2 | 34 ± 4 |
| 24-Dihomo-1,25-$(OH)_2$-22-dehydro-vitamin $D_3$ (compound 25) | $5 \times 10^{-8}$ M | 92 ± 2 | 93 ± 3 | 92 ± 2 |
| | $1 \times 10^{-8}$ M | 78 ± 4 | 77 ± 3 | 78 ± 3 |
| | $5 \times 10^{-9}$ M | 67 ± 4 | 69 ± 2 | 69 ± 3 |
| | $1 \times 10^{-9}$ M | 49 ± 2 | 50 ± 3 | 48 ± 3 |
| | $5 \times 10^{-10}$ M | 36 ± 4 | 36 ± 4 | 40 ± 3 |

Example 6

Calcemic activity of dihomo compound (25)

(a) Intestinal calcium transport activity (Table 2)

Male weanling rats were obtained from the Harlan-Sprague Dawley Company of Madison, Wis., and fed the low calcium, rachitogenic diet (0.02% Ca, 0.3% P) described by Suda et al. (J. Nutr. 100, 1049–1052, 1970). They were fed on this diet for a total of 4 weeks ad libitum. At the end of the third week the animals were divided into groups of 6 rats each. One group received a daily injection of vehicle (0.1 mL of 95% propylene glycol, 5% ethanol) interperitoneally for 7 days. The remaining groups received the same amount of vehicle over the same period of time but containing one of the following doses: 12.5 ng or 25 ng of 1,25-$(OH)_2D_3$ or 125 ng of 24- dihomo-1α,25-dihydroxy-22-dehydrovitamin $D_3$ (compound 25). The animals were killed 24 h after the last dose, the intestines removed, and the duodenal segments were used to measure intestinal calcium transport as described by Halloran and DeLuca (Arch. Biochem. Biophys. 208, 477–486, 1981). Results are given in Table 2.

TABLE 2

Intestinal Calcium Transport Activity of 1,25-$(OH)_2D_3$ and Side Chain Homolog in Rats

| Compound Administered | Amount (ng/d/7 days) | Ca Transport (Mean ± S.E.M.) |
|---|---|---|
| D-deficient (control) | 0 | 4.8 ± 0.2 |
| 1,25-$(OH)_2D_3$ | 12.5 | 11.2 ± 0.6 |
| | 25.0 | 13.4 ± 1.2 |

TABLE 2-continued

Intestinal Calcium Transport Activity of 1,25-$(OH)_2D_3$ and Side Chain Homolog in Rats

| Compound Administered | Amount (ng/d/7 days) | Ca Transport (Mean ± S.E.M.) |
|---|---|---|
| 24-Dihomo-1,25-$(OH)_2$-22-dehydrovitamin $D_3$ (compound 25) | 125.0 | 6.8 ± 0.45 |

(b) Measurement of bone calcium mobilization (Table 3)

Male weanling rats were obtained from the Harlan Sprague Dawley Company and fed the low calcium (0.02% Ca, 0.3% P) vitamin D-deficient diet described by Suda et al. (J. Nutr. 100, 1049–1052, 1970) for a period of 4 weeks. At the end of the third week the animals were divided into groups of 6 animals each and received the indicated doses (see Table 3) dissolved in 0.1 mL 95% propylene glycol and 5 ethanol. The control group received the solvent vehicle only. The other groups received the indicated dosage of 1,25-$(OH)_2D_3$ or the dihomo compound (25) each day for 7 days. Serum calcium was measured at the end of 7 days of dosing by atomic absorption. Results of two such experiments are given in Table 3 below.

TABLE 3

Bone Calcium Mobilization Activity (Serum Calcium Levels) of 1,25-$(OH)_2D_3$ and Side Chain Homolog in Rats

| Compound Administered | Amount (ng/d/7 days) | Serum Calcium (Mean ± S.E.M.) mg % | |
|---|---|---|---|
| | | Experiment 1 | Experiment 2 |
| D-Deficient (control) | 0 | 3.4 ± 0.07 | 4.1 ± 0.05 |
| 1,25-$(OH)_2D_3$ | 12.5 | 3.7 ± 0.17 | 4.8 ± 0.08 |
| | 25.0 | 4.1 ± 0.07 | 4.8 ± 0.08 |
| | 75.0 | 4.6 ± 0.09 | — |
| 24-Dihomo-1,25-$(OH)_2$-22-dehydrovitamin $D_3$ (Compound 25) | 25.0 | 3.6 ± 0.16 | — |
| | 125.0 | 3.7 ± 0.13 | 4.36 ± 0.15 |
| | 250.0 | 4.1 ± 0.05 | — |
| | 500.0 | 3.8 ± 0.11 | — |

The results presented in Table 1 clearly indicate that the dihomo analog 25 is distinctly more potent than 1,25-$(OH)_2D_3$ in inducing the differentiation of leukemic cells to normal monocyte cells. For example, at a concentration of $1 \times 10^{-8}$ molar, 1,25-$(OH)_2D_3$ produces 55–61% differentiated cells, whereas compound (25) at the same concentration gives 78% differentiation. Considering that a concentration of $1 \times 10^{-7}$ molar of 1,25-$(OH)_2D_3$ is required to achieve the same degree of differentiation (~90%), as produced by a concentration of $5 \times 10^{-8}$ molar of the dihomo analog (ca. 92%), one can conclude that the analog 25 is in the order of 5 times more potent than 1,25-$(OH)_2D_3$ as a differentiation agent.

In sharp contrast, the dihomo compound shows very low calcemic activity compared to 1,25-$(OH)_2D_3$. This conclusion is supported by the results of Tables 2 and 3. The intestinal calcium transport assay, represented by Table 2, for example, shows the known active metabolite, 1,25-$(OH)_2D_3$ to elicit, as expected, very pronounced responses (compared to control) when administered at doses of 12.5 or 25 ng/day for 7 days, In the case of the new dihomo compound (25), however, doses of 125 ng/day for 7 days are required to elicit a response, and even at such high dosage levels the response is modest, being slightly better than half that induced by 1,25-$(OH)_2D_3$ at a 10-fold lower dose. In this assay, therefore, the new dihomo analog is at least 10 times less active than 1,25-$(OH)_2D_3$.

The same conclusion can be drawn from the results of the bone calcium mobilization assay shown in Table 3. Here doses of 125 and 250 ng/day (administered for 7 days) of the dihomo analog (25) are required to achieve the same degree of response as that produced by 12.5 and 25 ng, respectively, of 1,25-$(OH)_2D_3$. Notable, too, is the fact that a further increase in the dose of the dihomo compound (to 500 ng/day) does not further increase, but, if anything supresses, the bone calcium mobilization response (see Table 3). In a second experiment—also tabulated in Table 3—in which 1,25-$(OH)_2D_3$ again elicited a very significant response (compared to control) at doses of 12.5 and 25 ng/day, the dihomo analog showed no activity at a dose of 125 ng/day. In a third experiment, in which the dihomo analog 25 was tested over a dosage range up to 1000 ng/day, the compound elicited no calcium mobilization response at any dose level, showing the material to be essentially without activity in raising serum calcium at the expense of bone. These bone mobilization assay, therefore, are in full accord with the calcium transport data of Table 2, and show clearly that the new dihomo analog 25 is many times less potent than 1,25-$(OH)_2D_3$ in its calcemic action.

The same type of activity pattern is observed for the trihomo compound 26 of this invention. This substance also exhibits a highly favorable and dramatically enhanced differentiation/calcemic activity ratio, by virtue of showing pronounced activity in inducing HL-60 cell differentiation, while eliciting no significant response (compared to control) on serum calcium levels in rats.

This type of activity pattern is, of course, exactly what is desired for a compound designed for use as a differentiation agent in the treatment of neoplastic diseases. The desired activity, the cellular differentiation of malignant cells, is highly pronounced, while the undesired activity, the calcemic action, is dramatically reduced, thus giving a very greatly enhanced differentiation/calcemic activity ratio. Known $1\alpha$-hydroxyvitamin D compounds have been shown to be effective therapeutic agents for the treatment of leukemic diseases (Suda et al., U.S. Pat. No. 4,391,802). Based on the bioassay data cited herein, one can conclude that the new side chain homo compounds of this invention, when administered at the same dosage level as the prior art compounds, would exhibit none or less than one-tenth of the undesired calcemic activity of the prior art compounds, thereby largely eliminating the problem of producing excessively elevated blood calcium levels in the treated subjects. Furthermore, based on the results presented in Table 1, one can expect the new homo compounds to exhibit a very high differentiation activity against malignant cells, especially leukemic cells, thus further enhancing their therapeutic benefit. Hence, the new compounds of this invention represent an effective practical embodiment of the concept of differentiation therapy of malignant diseases, and their activity patterns clearly suggest that they would be preferred therapeutic agents for such treatment.

For treatment purposes, these compounds can be formulated as solutions in innocuous solvents, or as emulsions, suspensions or dispersions in suitable and innocuous solvents or carriers, or as pills, tablets or capsules by conventional methods known in the art. Such formulations may also contain other pharmaceutically-acceptable and non-toxic excipients, such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal. For the treatment of human leukemia, the homovitamin D compounds of this invention are administered to subjects in dosages sufficient to induce the differentiation of leukemic cells to macrophages. Suitable dosage amounts are from 0.5 μg to 50 μg per day, it being understood that dosages can be adjusted (i.e. still further increased) according to the severity of the disease or the response or the condition of subject as well-understood in the art.

We claim:

1. Compounds having the structure

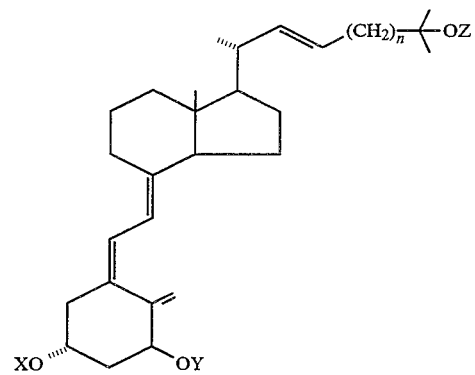

wherein X, Y and Z, which may be the same or different, are selected from the group consisting of hydrogen and a hydroxy-protecting group, and n is 3 or 4.

2. The compounds of claim 1 where each of X, Y and Z is hydrogen.

3. 24-dihomo-$1\alpha$,25-hydroxy-22-dehydrovitamin $D_3$.

4. 24-trihomo-$1\alpha$,25-dihydroxy-22-dehydrovitamin $D_3$.

5. Compounds having the structure

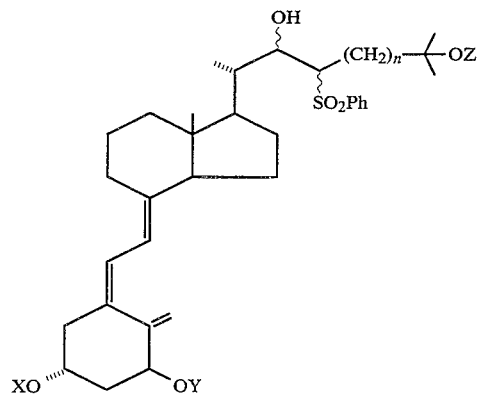

wherein X, Y and Z, which may be the same or different, are selected from the group consisting of hydrogen and a hydroxy-protecting group, and where n is 3 or 4.

6. A pharmaceutical composition containing at least one compound as claimed in claim 1 together with pharmaceutically acceptable excipients.

7. A pharmaceutical composition as claimed in claim 6 containing 24-dihomo-$1\alpha$,25-dihydroxy-22-dehydrovitamin $D_3$.

8. A pharmaceutical composition as claimed in claim 6 containing 24-trihomo-1α,25-dihydroxy-22-dehydrovitamin $D_3$.

9. A pharmaceutical composition as claimed in claim 7 claiming 24-dihomo-1α,25-dihydroxy-22-dehydrovitamin $D_3$ in an amount from about 0.5 μg to about 5 μg.

10. A pharmaceutical composition as claimed in claim 8 containing 24-trihomo-1α,25-dihydroxy-22-dehydrovitamin $D_3$ in an amount of about 0.5 to about 50 μg.

11. A method for inducing and enhancing cell differentiation in malignant cells while eliciting calcemic activity lower than 1α,25-dihydroxy-vitamin $D_3$ which comprises administering to said cells at least one 1α-hydroxyvitamin D homolog as claimed in claim 1.

12. The method of claim 11 where the 1α-hydroxyvitamin D homolog is 24-dihomo-1α,25-dihydroxy-22-dehydrovitamin $D_3$.

13. The method of claim 11 where the 1α-hydroxyvitamin D homolog is 24-trihomo-1α,25-dihydroxy-22-dehydrovitamin $D_3$.

14. A method for inhibiting proliferation of and for differentiating malignant cells of neoplastic diseases while eliciting calcemic activity lower than 1α,25-dihydroxy-vitamin $D_3$ which comprises administering to a subject having a neoplastic disease a dose of from about 0.5 to about 50 μg of a 1α-hydroxyvitamin D homolog as claimed in claim 1.

15. The method of claim 14 where the 1α-hydroxyvitamin D homolog administered is 24-dihomo-1,25-dihydroxy-22-dehydrovitamin $D_3$.

16. The method of claim 14 where the 1α-hydroxyvitamin D homolog administered is 24-trihomo-1,25-dihydroxy-22-dehydrovitamin $D_3$.

* * * * *

UNITED STATES PATENT AND TRADEMARK OFFICE
CERTIFICATE OF CORRECTION

PATENT NO. : 5,354,744
DATED : October 11, 1994
INVENTOR(S) : Hector F. DeLuca et al It is certified that error appears in the above-indentified patent and that said Letters Patent is hereby corrected as shown below:

IN THE CLAIMS:

Claim 3             Change "hydroxy" to ---dihydroxy---
Col. 20, line 39

Signed and Sealed this

Twenty-fifth Day of April, 1995

Attest:

BRUCE LEHMAN

Attesting Officer        *Commissioner of Patents and Trademarks*